(12) United States Patent
Resnati et al.

(10) Patent No.: US 9,932,316 B2
(45) Date of Patent: Apr. 3, 2018

(54) IMIDAZOLIUM SALTS HAVING LIQUID CRYSTAL CHARACTERISTICS, USEFUL AS ELECTROLYTES

(75) Inventors: Giuseppe Resnati, Monza (IT); Pierangelo Metrangolo, Pioltello (IT); Antonio Abate, Milan (IT); Francesco Matteucci, Ravenna (IT)

(73) Assignee: DAUNIA SOLAR CELL S.R.L., Foggia (IT)

( * ) Notice: Subject to any disclaimer, the term of this patent is extended or adjusted under 35 U.S.C. 154(b) by 1111 days.

(21) Appl. No.: 13/322,355

(22) PCT Filed: Jun. 10, 2010

(86) PCT No.: PCT/EP2010/003483
§ 371 (c)(1),
(2), (4) Date: Feb. 8, 2012

(87) PCT Pub. No.: WO2010/142445
PCT Pub. Date: Dec. 16, 2010

(65) Prior Publication Data
US 2012/0135316 A1 May 31, 2012

(30) Foreign Application Priority Data
Jun. 10, 2009 (EP) ..................... 09425227

(51) Int. Cl.
*C07D 233/54* (2006.01)
*C09K 19/04* (2006.01)
*H01G 9/025* (2006.01)

(52) U.S. Cl.
CPC ............ *C07D 233/54* (2013.01); *C09K 19/04* (2013.01)

(58) Field of Classification Search
CPC .............. C07D 233/54; C23C 18/1216; C23C 18/1283
See application file for complete search history.

(56) References Cited

U.S. PATENT DOCUMENTS

| | | | | |
|---|---|---|---|---|
| 7,528,287 B2 * | 5/2009 | Harmer | ............... | C08G 65/20 568/617 |
| 8,507,052 B2 * | 8/2013 | Pecinovsky et al. | ........ | 428/1.1 |
| 8,563,657 B2 * | 10/2013 | Hsiao | ............... | C07D 233/56 525/244 |
| 2007/0066822 A1 | 3/2007 | Harmer et al. | | |
| 2009/0105400 A1 * | 4/2009 | Komatsu et al. | ............ | 524/516 |

FOREIGN PATENT DOCUMENTS

| | | |
|---|---|---|
| DE | 19610908 | 9/1997 |
| JP | 2008130688 | 6/2008 |
| WO | 2007050491 | 5/2007 |

OTHER PUBLICATIONS

Merrigan et al. "New fluorous ionic liquids function as surfactants in conventional room-temperature ionic liquids" Chem. Commun. 2000, 20, 2051-2052.*
Scovazzo, P. "Determination of the upper limits, benchmarks, and critical properties for gas separations using stabilized room temperature ionic liquid membranes (SILMs) for the purpose of guiding future research" J. Mem. Sci. 2009, 343(1-2), 199-211 (published online Jul. 22, 2009).*
Bara et al. "Gas separations in fluoroalkyl-functionalized room-temperature ionic liquids using supported liquid membranes" Chem. Eng. J. 2009, 147, 43-50 (published online Nov. 21, 2008).*
Merrigan, T. L. et al. "New fluorous ionic liquids function as surfactants in conventional room-temperature ionic liquids" Chem. Commun. 2000, 20, 2051-2052.*
Matsubara et al. "Preparation of Fluorous DMF Solvents and Their Use for Some Pd-catalyzed Cross-coupling Reactions" Chem. Lett. 2005, 34, 1548-1549.*
Döbbelin et al. "Tuning Surface Wettability of Poly(3-sulfopropyl methacrylate) Brushes by Cationic Surfactant-Driven Interactions" Macromol. Rapid. Commun. 2008, 29, 871-875.*
Kysilka et al. "Fluorous imidazolium room-temperature ionic liquids based on HFPO trimer." J. Fluorine Chem. 2009, 130, 629-639 (Apr. 24, 2009).*
Lijin Xu, et al., Fluoroalkylated N-Heterocyclic Carbene . . . , Journal of Organometallic Chemistry, vol. 598, No. 2, 2000.

* cited by examiner

*Primary Examiner* — Amanda L Aguirre
(74) *Attorney, Agent, or Firm* — Lucas & Mercanti, LLP

(57) ABSTRACT

Novel imidazolium salts of formula (I) are described in which R is a $C_1$-$C_{14}$ alkyl group, optionally substituted by one or more fluorine atoms, or a $C_2$-$C_{18}$ alkoxyalkyl group, R' is an alkyl group containing at least 8 carbon atoms, at least 6 of which are partially or entirely fluorinated, R" is hydrogen or $C_1$-$C_3$ alkyl, Z is an organic or inorganic anion, and Q is further defined. The compounds of formula (I) are liquid crystals over a wide temperature range, and are characterized by high conductivity, hydrophobicity and stability. These properties made them ideally suitable for use in devices based on electrochemical reactions, such as solar cells, fuel cells, electrochemical sensors, lithium batteries and capacitors, etc.

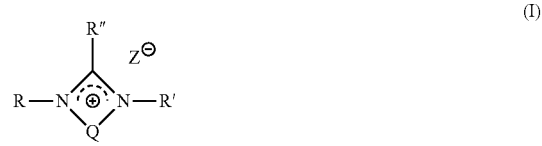

5 Claims, No Drawings

IMIDAZOLIUM SALTS HAVING LIQUID CRYSTAL CHARACTERISTICS, USEFUL AS ELECTROLYTES

CROSS-REFERENCE TO RELATED APPLICATIONS

This application is a 371 of PCT/EP2010/003483 filed on Jun. 10, 2010, which claims the benefit of European Patent Application No. 09425227.7 filed on Jun. 10, 2009, the contents of each of which are incorporated herein by reference.

DESCRIPTION

Field of the Invention

The present invention relates to the field of organic electrolytes and to the use thereof in electrical and/or electronic devices.

Prior Art

Organic electrolytes are commonly used as charge carriers in various items of electrical and electronic equipment such as double-layer electric capacitors, electrochemical cells, solar cells, fuel cells and electrochemical sensors, etc. In particular, ammonium salts and imidazolium salts are widely used: they are generally used in low viscosity solutions with appropriate solvents (e.g. lactones, nitriles and carbonates), often in the presence of iodine, which facilitates charge transfer by forming the redox pair I—/I$^3$—.

Fluorination is generally useful for increasing chemical stability; fluorinated imidazolium salts are described for example in JP 2002-260966; however, fluorination is only partially exploited because, beyond a limited number of fluorine atoms, the solubility of the electrolyte declines, resulting in reduced efficiency of the system.

EP1209707 describes polyfluoroalkylated ammonium salts: these salts exhibit good stability; electrical conductivity is said to increase in parallel with the concentration of the salts in solution; however, concentration also increases the viscosity of the solution, and this restricts the functionality of the system.

JP2008-130688 describes electrolyte solutions formed by imidazolium salts with poly- and perfluoroalkyl chains, dissolved in appropriate solvents; this document describes highly soluble products capable of forming low viscosity solutions, both of these characteristics being desired for good functioning of the electrolyte.

The above-described electrolyte solutions are subject to a loss of efficiency over time, which is brought about by the partial loss of solvent by evaporation; this loss may be particularly substantial in the case of use in solar panels, which reach temperatures of up to 90° C.; solvent losses bring about an increase in viscosity of the electrolyte solution and a consequent increase in internal resistance with dramatic reductions in device efficiency.

Some attempts to obtain electrolytes which function in the absence of solvent are also known. JP2005-179254 describes imidazolium salts with ionic liquid properties ("molten salts") made up of a cyclic, monofluoro-substituted ammonium cation: the conductivity demonstrated in the examples is slight (less than 0.1 mS cm$^{-1}$); the salts described in this document have a medium to low molecular weight (less than 200); among said salts, those cations with a higher molecular weight are stated to cause an increase in viscosity and a significant reduction in conductivity; in order to increase efficiency, the document suggests combining these compounds with similar non-fluorinated cations. It is stated in *The Electrochemical Society Interface*, Spring 2007, pp. 42-49 that hitherto identified ionic liquids exhibit problems of low conductivity and high viscosity. *J. Phys. Chem. B* 2007, 111, 4763-4769 describes non-fluorinated imidazolium salts; these compounds assume liquid crystal form over a restricted temperature range, said range being further reduced in the presence of iodine (*Electrochimica Acta*, 53 (2008), 2281-88).

The difficulty of reconciling electrolyte stability with electrolyte effectiveness is thus noted. This is because using high salt concentrations (necessary to increase conductivity) or a high level of fluorination (useful for stabilising the electrolyte molecule chemically), reduce the solubility of the salt and increase the viscosity of the solution, so reducing system efficiency; similarly, adding long-chain substituents (useful for increasing hydrophobicity and making the compound less hygroscopic and thus more stable) brings about a reduction in solubility with the above-stated adverse effects; furthermore, all systems based on electrolyte solutions are subject to the risk of increased viscosity and reduced efficiency due to solvent loss; on the other hand, research into electrolyte systems which might function efficiently in the absence of solvent has not hitherto yielded satisfactory results.

BRIEF DESCRIPTION OF THE INVENTION

We have surprisingly found novel imidazolium salts having liquid-crystalline properties over wide temperature ranges: these salts, alone or mixed with one another, function efficiently as electrolytes in the absence of solvent and provide a solution to the above-stated problems. The salts in question are represented by the formula (I)

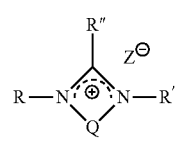

in which Q represents a —CRa=CRb- group, in which Ra and Rb independently represent H or methyl, or the —CRa=CRb- group is part of an optionally substituted fused aromatic or heteroaromatic cyclic system.
R is a $C_1$-$C_{14}$ alkyl group, optionally substituted by one or more fluorine atoms, or a $C_2$-$C_{18}$ alkoxyalkyl group.
R' is an alkyl group containing at least 8 carbon atoms, at least 6 of which are partially or entirely fluorinated.
R" is hydrogen or $C_1$-$C_3$ alkyl.
Z is an organic or inorganic anion.

The compounds of formula (I) exhibit a series of advantageous properties which make them ideally usable as electrolytes within electrical and/or electronic devices. In particular, they exhibit greater conductivity than has hitherto been obtained with liquid-crystalline electrolyte systems, together with excellent stability. Conductivity is furthermore independent of the viscosity of the system. An electrolyte system has accordingly been developed which operates satisfactorily even at elevated viscosity levels, as for example arise from extensive perfluorination or from an increase in the size of the alkyl chain of the electrolyte; thanks to these properties, the Applicant has been able fully to exploit the effect of a high level of perfluorination and of substitution with high molecular weight alkyl chains (useful for improving the stability of the electrolyte and of the device containing it), while maintaining adequate charge transfer efficiency; furthermore, the best conductivity values were surprisingly found precisely for those compounds substituted with longer alkyl chains, which are generally considered to perform less well because they impart greater viscosity. Another interesting and unexpected property of the compounds of formula (I) is the wide temperature range (80° C. on average, peaking at 130° C.) within which they aggregate in the form of liquid crystals; this range is particularly stable with regard to external factors: in particular, it does not narrow in the presence of iodine, a component which is essential for the functioning of many devices, in particular DSSC; conversely, the range of existence in liquid crystal form is reduced dramatically in the presence of iodine for other imidazolium compounds, even those organised in the form of liquid crystals, but which do not have the structure of the present formula (I). Finally, the liquid-crystalline structure allows the salts of formula (I) to function efficiently as electrolytes without the necessity of adding solvents: elimination of the risk of variation in effectiveness due to solvent content is also accompanied by greater simplicity of producing and managing the electrolyte system and the devices containing it.

DETAILED DESCRIPTION OF THE INVENTION

All the alkyl or alkoxyalkyl groups referred to here are understood to be either linear or branched; in relation to alkoxyalkyl groups, the indication $C_2$-$C_{18}$ refers to the overall number of carbon atoms present before and after the oxygen atom.

When R is alkyl, preferred meanings are: methyl, ethyl, propyl, isopropyl, butyl, pentyl, hexyl, octyl, nonyl, decyl, dodecyl, tetradecyl, and the isomers thereof; linear-chain propyl, butyl, pentyl, hexyl, octyl, decyl, dodecyl are preferred; linear-chain propyl, butyl, pentyl, hexyl, heptyl, octyl are particularly preferred.

When R is fluoro-substituted alkyl, preferred meanings are: $CF_2H$—$CFHCFH$—, $CF_3CH_2CH_2$—, $C_2F_5CH_2CH_2$, $CF_3CH_2CH_2CH_2CH_2$—; $CF_3$— and $CF_3CH_2CH_2$—.

When R is alkoxyalkyl, preferred meanings are: methoxymethyl, methoxyethyl, methoxypropyl, butoxypropyl.

The group R' preferably contains from 8 to 18 carbon atoms, e.g. from 8 to 14. The carbon atoms of R' involved in fluorination are preferably completely fluorinated; furthermore, they are preferably contiguous with one another and make up the terminal portion of the R' group (i.e. the portion farther from the imidazolium ring); the carbon atoms of R' which are not involved in fluorination, if present, are preferably contiguous with one another and make up the proximal portion of R' (i.e. the portion closest to the imidazolium ring).

Particularly preferred meanings of R' (in which the fluorinated part is highlighted) are:
$CF_3CF_2CF_2CF_2CF_2CF_2CH_2CH_2$—,
$CF_3CF_2CF_2CF_2CF_2CF_2CH_2CH_2CH_2$—,
$CF_3CF_2CF_2CF_2CF_2CF_2CF_2CH_2CH_2$—,
$CF_3CF_2CF_2CF_2CF_2CF_2CF_2CH_2CH_2CH_2$—,
$CF_3CF_2CF_2CF_2CF_2CF_2CF_2CF_2CH_2CH_2$—,
$CF_3CF_2CF_2CF_2CF_2CF_2CF_2CF_2CH_2CH_2CH_2$—.

The anion Z— is preferably selected from among Cl—, Br—, I—, $AlCl_4$—, $BF_4$—, $PF_6$—, $AsF_6$—, $TaF_6$—, $SbF_6$—, $CF_3COO$—, $CF_3SO_3$—, $(CF_3SO_2)_2N$—, $(C_2F_5SO_2)_2N$—. The fused aromatic or heteroaromatic cyclic system which comprises the —CRa=CRb- group may be selected from among any commonly known aromatic/heteroaromatic structures, e.g. phenyl, naphthyl, pyridine, pyrazine, pyridazine, pyrrole, etc.: the substituents optionally present on said cyclic systems are preferably selected from among alkyl groups.

The dashed line in formula (I) indicates that the positively charged quaternised nitrogen may be either of the nitrogens which are part of the imidazolium ring, in accordance with one of the two structures:

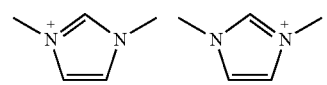

The compounds of formula (I) are particularly effective when substituted with longer alkyl chains R and/or R', corresponding to a greater degree of hydrophobisation and, surprisingly, to higher conductivity. The substituent R" primarily contributes to stabilisation, —$CH_3$ being particularly preferred in this position.

Preferred compounds of formula (I) generally exhibit a molecular weight of between 300 and 1000, preferably of between 400 and 900, more preferably of between 500 and 800.

Specific preferred compounds in accordance with the present invention are those in which:

| R | R" | R' |
|---|---|---|
| $CH_3$— | H— | —$(CH_2)_2$—$(CF_2)_5$—$CF_3$ |
| $CH_3$— | H— | —$(CH_2)_3$—$(CF_2)_5$—$CF_3$ |
| $CH_3$—$(CH_2)_9$— | H— | —$(CH_2)_3$—$(CF_2)_5$—$CF_3$ |
| $CH_3$—$(CH_2)_{11}$— | H— | —$(CH_2)_3$—$(CF_2)_5$—$CF_3$ |
| $CH_3$— | $CH_3$— | —$(CH_2)_3$—$(CF_2)_5$—$CF_3$ |
| $CH_3$—$(CH_2)_7$— | H— | —$(CH_2)_3$—$(CF_2)_5$—$CF_3$ |
| $CH_3$—$(CH_2)_5$— | H— | —$(CH_2)_3$—$(CF_2)_5$—$CF_3$ |
| $CH_3$—$(CH_2)_5$— | H— | —$(CH_2)_3$—$(CF_2)_5$—$CF_3$ |

The invention in particular relates to compounds of formula (I) characterised by a liquid crystal structure. Liquid crystal texture is detectable by means of standard methods, in particular differential scanning calorimetric analysis (DSC) and polarising optical microscopy (POM), as known in the field; the temperature range which determines the liquid-crystalline phase extends between the DSC peak corresponding to the melting point and that corresponding to the transition to the isotropic form (clearing point). The liquid-crystalline structure is then characterised by means of POM; liquid-crystalline aggregation for compounds of formula (I) is preferably of the smectic A type.

The wide and stable temperature range which characterises the existence of the present compounds in liquid crystal form makes them suitable for the production of electrochemical devices which operate under the most varied ambient conditions and are unaffected by variation of such conditions. The experimental testing described here has furthermore demonstrated that the temperature range which determines the liquid-crystalline state remains substantially unchanged in the presence of iodine and/or iodine salts, unlike the situation observed for other molecules of a similar structure.

The above-stated advantages are reflected in a substantial functional improvement (elevated efficiency and stability) in the devices containing the electrolytes of the invention. The invention thus includes the devices as such, of elevated stability and efficiency, characterised by containing one or more electrolytes of formula (I) as previously defined. Such devices are for example electrochemical cells, solar cells such as e.g. dye-sensitised solar cells (DSSC), fuel cells, electrochemical sensors, lithium batteries and capacitors. Particular benefits are achieved by devices which use iodine as a mediator, e.g. DSSC. With regard to the manufacture of the devices themselves and to the introduction of the electrolyte, reference is made to known methods commonly used in the field.

The present invention also relates to the use of the compounds of formula (I), alone or mixed with one another, as electrolytes with high conductivity, hydrophobicity and chemical stability for use in electrochemical cells, solar cells such as dye-sensitised solar cells, fuel cells, electrochemical sensors, lithium batteries and capacitors. Such compounds are preferably used in the absence of solvent.

The present invention furthermore provides a method for preparing the compounds of formula (I). The latter may be obtained by reacting an appropriate compound of formula (II):

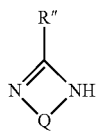

(II)

with an alkyl halide of formula RZ, in which Q, R″, R and Z have the above-defined meanings, in the presence of an appropriate inorganic base (such as e.g. KOH) and an appropriate organic solvent (such as e.g. acetonitrile). Alkylation conditions are preferably as follows: reaction time of between 4 and 12 hours, organic solvent selected from among $C_1$-$C_4$ alcohols such as for example methanol, ethanol, propanol, isopropanol, butanol and the isomers thereof, alkyl or alicyclic ethers such as for example diisopropyl ether, tetrahydrofuran, methyltetrahydrofuran, dioxane, alkyl nitriles such as for example acetonitrile, propionitrile, methoxypropionitrile, aromatic solvents such as, for example, toluene, xylene, chlorinated solvents such as, for example, dichloromethane, chloroform, dichloroethane; methanol, isopropanol, tetrahydrofuran, toluene, acetonitrile are preferred; acetonitrile is particularly preferred. The alkylation reaction is preferentially carried out at the reflux temperature of the solvent. In another step, the monoalkylation reaction product is reacted with a second fluorinated alkyl halide of formula R′Z, in which R′ has the above-defined meanings. The reaction conditions are preferably as follows: reaction time of between 10 and 16 hours, organic solvent selected from among alkyl or alicyclic ethers such as for example diisopropyl ether, tetrahydrofuran, methyltetrahydrofuran, dioxane, aromatic solvents such as, for example, toluene, xylene; tetrahydrofuran and toluene are preferred; toluene is particularly preferred. The alkylation reaction is preferentially carried out at the reflux temperature of the solvent. In the present process, the order in which the two positions are alkylated is purely indicative and can be reversed without going beyond the scope of the present invention.

In a non-exclusive embodiment, the method is defined by the following scheme:

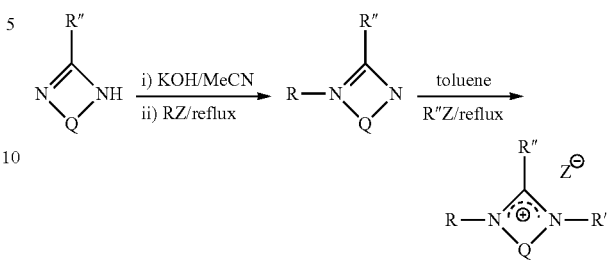

The starting compounds of formula (II) are commercially available or may readily be synthesised using methods described in the literature.

The invention is described below by means of the following examples which are not limiting in nature.

EXPERIMENTAL SECTION

General Synthesis Method
Imidazole Alkylation

An aqueous 4M solution of potassium hydroxide (2 equivalents per equivalent of 1H-imidazole) is added to a solution of 1H-imidazole in acetonitrile (1 mmol per 0.6 ml of solvent); the solution is stirred for 2 hours at room temperature. 2 equivalents of alkyl iodide (RI) per equivalent of 1H-imidazole are then added and the mixture is heated to reflux for 12 hours. The mixture is then cooled to room temperature and evaporated under vacuum (30° C./18 mbar). The residue is resuspended with a saturated aqueous NaCl solution and extracted three times with dichloromethane. The three organic fractions are combined, dried by means of $Na_2SO_4$ and the solvent evaporated under vacuum at 25° C./18 mbar. The resultant residue composed of 1-alkyl-1H-imidazole is used for the second alkylation step.
Alkylation (perfluoroalkylation) of 1-alkyl-1H-imidazole The previously obtained 1-alkyl-1H-imidazole is quaternised with an equimolar quantity of the corresponding fluoroalkyl iodide (RI) by heating to reflux for 12 hours in toluene.
Characterisation The products are identified by means of $^1H$ and $^{19}F$ NMR using $CDCl_3$ as solvent, differential scanning calorimetry (DSC) and polarising optical microscopy (POM). The electrolyte is prepared by mixing the fluorinated imidazolium iodide with iodine in a 1:10 ratio (mol/mol), without adding other additives.
Thermal Investigations Thermal transitions were determined by means of DSC (under a stream of nitrogen), heating and cooling at a rate of 10° C./min. In all cases, a typical DSC trace exhibits a characteristic wide enthalpy for the crystal/crystal liquid transition and a small enthalpy for the mesophase/isotropic transition. The mesophase transition temperatures were also determined by means of observations by polarising optical microscopy at a controlled temperature.
Photoelectrochemical Measurements Electrical conductivity was measured by means of electrical impedance spectroscopy (EIS). The EIS spectrum was recorded between the frequencies of 1 MHz and 0.1 Hz at room temperature. Special electrodes made of a thin film of platinum (10 μm) deposited on a glass substrate were used to assess the anisotropic component of conductivity along the direction of the smectic planes. Homeotropic alignment in the smectic A phases during the measurements was confirmed by observations made under a polarising light optical microscope.

Photoelectrochemical cells were manufactured to measure the efficiency of conversion of light into electrical current. A colloidal suspension of $TiO_2$ particles was deposited onto a transparent conductive substrate (F-doped $SnO_2$ glass). The electrodes were sintered at 450° C. for 30 min in air. The resultant $TiO_2$ films (thickness 10 micrometers) were immersed in $5.0 \cdot 10^{-4}$ M cis-dithiocyanate-N,N'-bis(4-carboxylate-4-tetrabutylammoniumcarboxylate-2,2'-bipyridine) ruthenium(II) in a (1:1) solution of acetonitrile/2-methyl-2-propanol for 24 h. After drying the electrode, the porous surface was covered with platinised conductive glass as the counter-electrode. The effective area of the cell electrode was 0.20 cm$^2$. The electrolytes composed of the fluorinated imidazolium iodides and iodine were injected in the space between the electrodes, the temperature being maintained at 80° C. The efficiency of conversion of light into electricity was evaluated at room temperature using a solar simulator as AM 1.5 light source and a PC-controlled multimeter.

Synthesis and Characterisation of Compounds of Formula (I)

Example 1

Synthesis of 1-methyl-3-(8,8,8,7,7,6,6,5,5,4,4,3,3-tridecafluorooctan-1-yl)-1H-imidazolium iodide 0.39 g (4.75 mmol) of 1-methyl-1H-imidazole is dissolved in 7 ml of toluene and 1.31 g (5.36 mmol) of 1,1,1,2,2,3,3,4,4,5,5,6,6-tridecafluoro-8-iodooctane are added. The mixture is heated to reflux for 12 hours, cooled and evaporated under vacuum (35° C./18 mbar). The resultant residue is resuspended with a 1:1 vol./vol. solution (5 ml) of acetonitrile/chloroform and purified on a silica gel column.

A solid is obtained by evaporation, which is characterised as stated below.

$^1$H-NMR (250 MHz, DMSO): δ=9.188 (s, 1H), 7.863 (s, 1H), 7.713 (s, 1H), 4.566 (t, 2H, J=6.539 Hz), 3.072 (s, 3H), 3.006 (m, 2H)

$^{19}$F-NMR (235 MHz, DMSO): δ=−80.732 (t, 3F, J=9.155 Hz), −113.629 (m, 2F), −122.135 (m, 2F), −123.085 (m, 2F), −123.650 (m, 2F), −126.201 (m, 2F)

ESI-MS, positive ion mode: m/z 429

DSC: heating and cooling at a rate of 10° C. min$^{-1}$

| Melting (° C.) | LC phase | Clearing (° C.) |
| --- | --- | --- |
| 94 | ↔ | 223 |

FT-IR (4000-600 cm$^{-1}$ range): 3418, 3057, 1233, 1179, 1142, 1079, 692, 661, 614 cm$^{-1}$ Example 2

Synthesis of 1-methyl-3-(9,9,9,8,8,7,7,6,6,5,5,4,4-tridecafluorononan-1-yl)-1H-imidazolium iodide In a similar manner to that stated in Example 1, 0.151 g (1.84 mmol) of 1-methyl-1H-imidazole is dissolved in 4 ml of toluene and 0.98 g (2.02 mmol) of 1,1,1,2,2,3,3,4,4,5,5,6,6-tridecafluoro-9-iodononane is added. The mixture is heated to reflux for 12 hours, cooled and evaporated under vacuum (35° C./18 mbar). The resultant residue is recrystallised from 10:1 vol./vol. solution (10 ml) of dichloromethane/ethyl ether.

A solid is obtained by evaporation, which is characterised as stated below.

$^1$H-NMR (250 MHz, MeOD): δ=9.246 (s, 1H), 7.852 (s, 1H), 7.725 (s, 1H), 4.512 (t, 2H, J=7.535 Hz), 4.036 (m, 3H), 2.305 (m, 4H)

$^{19}$F-NMR (235 MHz, MeOD): δ=−83.186 (t, 3F, J=10.681 Hz), −115.507 (m, 2F), −123.439 (m, 2F), −124.487 (m, 2F), −124.756 (m, 2F), −127.985 (m, 2F)

ESI-MS, positive ion mode: m/z 443

DSC: heating and cooling at a rate of 10° C. min$^{-1}$

| Melting (° C.) | LC phase | Clearing (° C.) |
| --- | --- | --- |
| 86 | ↔ | 198 |

FT-IR (4000-600 cm$^{-1}$ range): 3081, 1243, 1173, 1141, 1082, 696, 652, 617 cm$^{-1}$ Example 3

Synthesis of 1-decyl-3-(9,9,9,8,8,7,7,6,6,5,5,4,4-tridecafluorononan-1-yl)-1H-imidazolium iodide In a similar manner to that stated in Example 1, 0.074 g (0.36 mmol) of 1-decyl-1H-imidazole is dissolved in 1 ml of toluene and 0.184 g (0.378 mmol) of 1,1,1,2,2,3,3,4,4,5,5,6,6-tridecafluoro-9-iodononane is added. The mixture is heated to reflux for 12 hours, cooled and evaporated under vacuum (35° C./18 mbar). The resultant residue is resuspended with a 96:4 vol./vol. solution (2 ml) of chloroform/methanol and purified on a silica gel column.

A solid is obtained by evaporation, which is characterised as stated below.

$^1$H-NMR (250 MHz, DMSO): δ=9.199 (s, 1H), 8.297 (s, 1H), 7.825 (s, 1H), 4.291 (t, 2H, J=7.357 Hz), 4.164 (t, 2H, J=7.084 Hz), 2.307 (m, 2H), 2.120 (m, 2H), 1.796 (m, 2H), 1.236 (s, 14H), 0.852 (t, 3H, 5.995 Hz)

$^{19}$F-NMR (235 MHz, DMSO): δ=−80.731 (t, 3F, J=9.155 Hz), −113.627 (m, 2F), −122.132 (m, 2F), −123.086 (m, 2F), −123.647 (m, 2F), −126.209 m, 2F)

DSC: heating and cooling at a rate of 10° C. min$^{-1}$

| Melting (° C.) | LC phase | Clearing (° C.) |
| --- | --- | --- |
| 74 | ↔ | 154 |

Example 4

Synthesis of 1-dodecyl-3-(9,9,9,8,8,7,7,6,6,5,5,4,4-tridecafluorononan-1-yl)-1H-imidazolium iodide In a similar manner to that stated in Example 1, 0.389 g (1.64 mmol) of 1-dodecyl-1H-imidazole is dissolved in 2 ml of toluene and 0.884 g (1.81 mmol) of 1,1,1,2,2,3,3,4,4,5,5,6,6-tridecafluoro-9-iodononane is added. The mixture is heated to reflux for 12 hours, cooled and evaporated under vacuum (35° C./18 mbar). The resultant residue is resuspended with a 90:10 vol./vol. solution (5 ml) of chloroform/methanol and purified on a silica gel column.

A solid is obtained by evaporation, which is characterised as stated below.

$^{1}$H-NMR (250 MHz, CDCl$_{3}$): δ=10.585 (s, 1H), 7.377 (s, 1H), 4.623 (t, 2H, J=7.067 Hz), 4.298 (t, 2H, J=7.710 Hz), 2.344 (m, 4H), 2.972 (m, 2H), 1.257 (m, 20H), 0.881 (t, 3H, J=6.746 Hz)

$^{19}$F-NMR (235 MHz, CDCl$_{3}$): δ=−81.336 (t, 3F, J=9.918 Hz), −114.068 (m, 2F), −122.335 (m, 2F), −123.344 (m, 2F), −123.679 (m, 2F), −126.608 m, 2F)

DSC: heating and cooling at a rate of 10° C. min$^{-1}$

| Melting (° C.) | LC phase | Clearing (° C.) |
|---|---|---|
| 77 | ↔ | 160 |

Example 5

Synthesis of 1-octyl-3-(9,9,9,8,8,7,7,6,6,5,5,4,4-tridecafluorononan-1-yl)-1H-imidazolium iodide In a similar manner to that stated in Example 1, 0.179 g (0.99 mmol) of 1-octyl-1H-imidazole is dissolved in 1 ml of toluene and 0.53 g (1.09 mmol) of 1,1,1,2,2,3,3,4,4,5,5,6,6-tridecafluoro-9-iodononane is added. The mixture is heated to reflux for 12 hours, cooled and evaporated under vacuum (35° C./18 mbar). The resultant residue is resuspended with dichloromethane and hexane and re-evaporated under vacuum (35° C./18 mbar).

A solid is obtained by further evaporation, which is characterised as stated below.

$^{1}$H-NMR (250 MHz, CDCl$_{3}$): δ=10.334 (s, 1H), 7.526 (s, 1H), 7.347 (s, 1H), 4.636 (t, 2H, J=7.324 Hz), 4.312 (t, 2H, J=7.629 Hz), 2.315 (m, 4H), 1.980 (m, 2H), 1.265 (m, 8H), 0.877 (t, 3H, J=6.104 Hz)

$^{19}$F-NMR (235 MHz, CDCl$_{3}$): δ=−81.335 (t, 3F, J=9.917 Hz), −114.066 (m, 2F), −122.337 (m, 2F), −123.343 (m, 2F), −123.676 (m, 2F), −126.604 (m, 2F)

DSC: heating and cooling at a rate of 10° C. min$^{-1}$

| Melting (° C.) | LC phase | Clearing (° C.) |
|---|---|---|
| 45 | ↔ | 107 |

Example 6

Synthesis of 1-hexyl-3-(9,9,9,8,8,7,7,6,6,5,5,4,4-tridecafluorononan-1-yl)-1H-imidazolium iodide In a similar manner to that stated in Example 1, 0.133 g (0.87 mmol) of 1-hexyl-1H-imidazole is dissolved in 1 ml of toluene and 0.449 g (0.92 mmol) of 1,1,1,2,2,3,3,4,4,5,5,6,6-tridecafluoro-9-iodononane is added. The mixture is heated to reflux for 12 hours, cooled and evaporated under vacuum (35° C./18 mbar).

A brown viscous oil is obtained by evaporation, which is characterised as stated below.

$^{1}$H-NMR (250 MHz, CDCl$_{3}$): δ=10.257 (s, 1H), 7.649 (s, 1H), 7.426 (s, 1H), 4.620 (t, 2H, J=6.746 Hz), 4.304 (t, 2H, J=7.710 Hz), 2.337 (m, 4H), 1.938 (m, 2H), 1.326 (m, 6H), 0.866 (t, 3H, J=7.388 Hz)

$^{19}$F-NMR (235 MHz, CDCl$_{3}$): δ=−81.332 (t, 3F, J=9.915 Hz), −114.064 (m, 2F), −122.337 (m, 2F), −123.342 (m, 2F), −123.675 (m, 2F), −126.603 (m, 2F)

DSC: heating and cooling at a rate of 10° C. min$^{-1}$

| Melting (° C.) | LC phase | Clearing (° C.) |
|---|---|---|
| −30 | ↔ | 37 |

Example 7

Synthesis of 1-hexyl-3-(10,10,10,9,9,8,8,7,7,6,6,5,5,4,4,3,3,-heptadecafluorodecan-1-yl)-1H-imidazolium iodide In a similar manner to that stated in Example 1, 0.3 g (1.97 mmol) of 1-hexyl-1H-imidazole is dissolved in 2 ml of toluene and 1.18 g (2.07 mmol) of 1,1,1,2,2,3,3,4,4,5,5,6,6,7,7,8,8-eptadecafluoro-10-iododecane are added. The mixture is heated to reflux for 12 hours, cooled and evaporated under vacuum (35° C./18 mbar).

A brown solid is obtained by evaporation, which is characterised as stated below.

$^{1}$H-NMR (250 MHz, CDCl$_{3}$): δ=10.436 (s, 1H), 7.458 (s, 1H), 4.907 (t, 2H, J=6.714 Hz), 4.290 (t, 2H, J=7.629 Hz), 2.969 (m, 2H), 1.964 (m, 2H), 1.336 (m, 6H), 0.885 (t, 3H, J=6.714 Hz)

$^{19}$F-NMR (235 MHz, CDCl$_{3}$): δ=−81.866 (t, 3F, J=10.729 Hz), −114.145 (m, 2F), −122.858 (m, 2F), −123.685 (m, 2F), −124.029 (m, 2F), −127.089 (m, 2F)

DSC: heating and cooling at a rate of 10° C. min$^{-1}$

| Melting (° C.) | LC phase | Clearing (° C.) |
|---|---|---|
| 90 | ↔ | 192 |

Liquid-Crystalline Properties in the Presence of Iodine

With reference to the general formula (I)

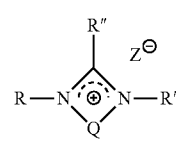

(I)

the following stability tests of the liquid-crystalline (LC) phase were carried out after addition of iodine:

| Example | R | R' | R" | Q | Melting (° C.) | LC phase | Clearing (° C.) | Eq. I$_2$ |
|---|---|---|---|---|---|---|---|---|
| a | —CH$_3$ | —(CH$_2$)$_2$(CF$_2$)$_6$F | H | —CH=CH— | 94 | ↔ | 223 | 0 |
|   | —CH$_3$ | —(CH$_2$)$_2$(CF$_2$)$_6$F | H | —CH=CH— | 89 | ↔ | 209 | 0.1 |
| b | —CH$_3$ | —(CH$_2$)$_{12}$H | H | —CH=CH— | 29 | ↔ | 82 | 0 |
|   | —CH$_3$ | —(CH$_2$)$_{12}$H | H | —CH=CH— | 34 | ↔ | # | 0.1 |

It can be noted that the compound shown as Example 1 of the invention (example "a" in the table above) exhibits a LC phase range which is virtually unchanged after the addition of 0.1 equivalents of iodine; conversely, in the example "b" compound in the table, a similar non-fluorinated molecule known from the literature (J. Phys. Chem. 2007, op.cit.), the LC phase disappears after adding the same number of equivalents of iodine. These and other tests carried out by the inventors demonstrate that the compounds of formula (I) according to the invention exhibit a range of liquid crystallinity which remains stable after the addition of iodine.

Mixtures of different salts of formula (I) were also prepared with the aim of modifying the range of existence in the liquid-crystalline state, for example making the range suitable for specific conditions of use. The temperature range proved to be readily controllable by varying the relative amount of the different components. It is readily possible to obtain mixtures with a wider range of existence in the liquid-crystalline state, in which the melting point aims towards that of the compound with the lower melting point, and the clearing point aims towards that of the compound with the higher clearing point. In this manner, products having liquid-crystalline properties over a wider temperature range, including ambient temperature, are readily obtained. Examples of mixtures prepared in this manner are as follows:

| 1:1 ratio (mol/mol) | Cr | T (° C.) | LC | T (° C.) | Iso |
|---|---|---|---|---|---|
| $C_6ImCH_2CH_2CH_2R_6f$ $C_8ImCH_2CH_2CH_2R_6f$ | ← | −25 | ↔ | 75 | → |
| $C_6ImCH_2CH_2CH_2R_6f$ $C_{10}ImCH_2CH_2CH_2R_6f$ | ← | −26 | ↔ | 107 | → |
| $C_1ImCH_2CH_2CH_2R_6f$ $C_6ImCH_2CH_2CH_2R_6f$ | ← | −26 | ↔ | 76 | → |

The salts from Examples 6 and 7 were used in the first mixture. The salts from Examples 6 and 3 were used in the second mixture. The salts from Examples 2 and 6 were used in the third mixture. Further testing of the stability of the liquid-crystalline phase in the presence of iodine was carried out on these mixtures; observations under a polarising light microscope revealed that the samples in the table stably maintain the LC phase even after the addition of iodine.

Electrochemical Properties

The liquid-crystalline electrolyte mixture containing the compounds of formula (I) described in Examples 6 and 7 in a 1:1 ratio (mol/mol) exhibited electrical conductivity of 0.5 mS cm$^{-1}$. The literature mentions electrical conductivity values of below 0.1 mS cm$^{-1}$ for similar liquid-crystalline electrolyte mixtures (JP2005-179254, op.cit.).

The unsolvated electrolyte mixture containing the compounds of formula (I) described in Examples 6 and 7 in 1:1 ratio (mol/mol) was used to assemble photoelectrochemical cells using the method described above. Preliminary measurements of the efficiency of conversion of light into electricity revealed values comparable with those stated in the relevant literature for unsolvated electrolytes.

Example 8

Synthesis of 1,2-dimethyl-3-(4,4,5,5,6,6,7,7,8,8,9,9,9-tridecafluoro-nonyl)-1H-imidazol-3-ium Iodide 0.3 g (3.121 mmol) of 1,2-dimethyl-1H-imidazole are dissolved in 5 ml of toluene and added with 1.675 g (3.43 mmol) of 1,1,1,2,2,3,3,4,4,5,5,6,6-tridecafluoro-9-iodononane. The mixture is reflux-heated for 24 hrs, then cooled and evaporated under vacuum (35° C./18 mbar). The residue is resuspended with a 95/5 v/v dichloromethane/methanol solution (10 ml) and recrystallized by addition of ethyl ether. The white solid recovered by filtration is left under vacuum for at least 24 hrs (25° C./18 mbar). The product is characterized as follows:

1H-NMR (250 MHz, DMSO): δ=7.692 (s, 1H), 7.633 (s, 1H), 4.233 (t, 2H, J=7.016 Hz), 3.749 (s, 3H), 2.595 (s, 3H), 2.377 (m, 2H), 2.011 (m, 2H)

19F-NMR (235 MHz, DMSO): δ=−80.733 (t, 3F, J=9.155 Hz), −113.631 (m, 2F), −122.131 (m, 2F), −123.086 (m, 2F), −123.653 (m, 2F), −126.204 (m, 2F)

ESI-MS, positive ion mode: m/z 457

DSC: heating and cooling at a rate of 10° C. min$^{-1}$

| Melting (° C.) | LC Phase | Clearing (° C.) |
|---|---|---|
| 192 | ↔ | 217 |

The stability of this molecule in presence of iodine was measured by comparison with a reference molecule of formula (I), where R is methyl, R' is n-propyl, and R" is hydrogen: this reference molecule is a well-known imidazolium salt, widely used in the art as an electrolyte for DSSC.

In presence of high alkali concentration and molecular iodine, the reference molecule partly degraded to a white solid product in which the hydrogen in R" is replaced by iodine, as confirmed by $_1$H-NMR and ESI-MS analysis.

1-methyl-3-propyl-1H-imidazol-3-ium iodide (R=methyl, R'=n-propyl, R"=hydrogen)

1H-NMR (250 MHz, DMSO): δ=9.096 (s, 1H), 7.751 (s, 1H), 7.693 (s, 1H), 4.125 (m, 2H), 3.852 (s, 3H), 1.812 (m, 2H), 0.858 (m, 3H)

ESI-MS, positive ion mode: m/z 125

2-Iodo-3-methyl-1-propyl-3H-imidazol-1-ium iodide (R=methyl, R'=n-propyl, R"=iodine)

1H-NMR (250 MHz, DMSO): δ=7.938 (m, 2H), 4.120 (m, 2H), 3.829 (s, 3H), 1.812 (m, 2H), 0.858 (m, 3H)

ESI-MS, positive ion mode: m/z 252

The formation of the above 2-iodo degradation product, scarcely soluble in the commonly used solvents, limits the performance of the reference electrolyte. A parallel experiment run on the invention product of Example 8 showed no formation of the 2-iodo derivative, i.e. the product of Example 8 remained stable in its original form even in the presence of iodine and alkali.

The invention claimed is:

1. Imidazolium salts having the structural formula (I)

(I)

or mixtures thereof, in which:
- Q represents a —CRa=CRb- group, in which Ra and Rb independently represent H or methyl;
- R is selected from the group consisting of ethyl, propyl, isopropyl, butyl, pentyl, hexyl, octyl, nonyl, decyl, dodecyl, tetradecyl, methoxymethyl, methoxyethyl, methoxypropyl, and butoxypropyl;

R' is selected from the group consisting of:
$CF_3CF_2CF_2CF_2CF_2CF_2CH_2CH_2$—,
$CF_3CF_2CF_2CF_2CF_2CF_2CH_2CH_2CH_2$—,
$CF_3CF_2CF_2CF_2CF_2CF_2CF_2CF_2CH_2CH_2$—,
$CF_3CF_2CF_2CF_2CF_2CF_2CF_2CF_2CH_2CH_2CH_2$—,
$CF_3CF_2CF_2CF_2CF_2CF_2CF_2CF_2CF_2CF_2CH_2CH_2$—, and
$CF_3CF_2CF_2CF_2CF_2CF_2CF_2CF_2CF_2CF_2CH_2CH_2CH_2$—,
with the proviso that, when R is propyl, butyl or pentyl, R' is not a group
$CF_3CF_2CF_2CF_2CF_2CF_2CH_2CH_2CH_2$—;
R" is hydrogen or $C_1$-$C_3$ alkyl;
Z is $Cl^-$, $Br^-$, $I^-$, $BF_4^-$, $CF_3SO_3^-$, or $(CF_3SO_2)_2N^-$; and
R, R', and R" are unsubstituted.

2. The salts according to claim 1, selected from among those compounds in which R, R", and R' are as follows:

| R | R" | R' |
|---|---|---|
| $CH_3$—$(CH_2)_9$— | H— | —$(CH_2)_3$—$(CF_2)_5$—$CF_3$ |
| $CH_3$—$(CH_2)_{11}$— | H— | —$(CH_2)_3$—$(CF_2)_5$—$CF_3$ |
| $CH_3$—$(CH_2)_7$— | H— | —$(CH_2)_3$—$(CF_2)_5$—$CF_3$ |
| $CH_3$—$(CH_2)_5$— | H— | —$(CH_2)_3$—$(CF_2)_5$—$CF_3$ |
| $CH_3$—$(CH_2)_5$— | H— | —$(CH_2)_2$—$(CF_2)_7$—$CF_3$. |

3. The salts according to claim 1, wherein the salts are in a liquid crystal form.

4. Imidazolium salts having the structural formula (I)

or mixtures thereof, in which:
Q represents a —CRa=CRb- group, in which Ra and Rb independently represent H or methyl;
R is a $C_2$-$C_{18}$ alkoxyalkyl group;
R' is selected from the group consisting of:
$CF_3CF_2CF_2CF_2CF_2CF_2CH_2CH_2$—,
$CF_3CF_2CF_2CF_2CF_2CF_2CH_2CH_2CH_2$—,
$CF_3CF_2CF_2CF_2CF_2CF_2CF_2CF_2CH_2CH_2$—,
$CF_3CF_2CF_2CF_2CF_2CF_2CF_2CF_2CH_2CH_2CH_2$—,
$CF_3CF_2CF_2CF_2CF_2CF_2CF_2CF_2CF_2CF_2CH_2CH_2$—, and
$CF_3CF_2CF_2CF_2CF_2CF_2CF_2CF_2CF_2CF_2CH_2CH_2CH_2$—;
R" is hydrogen or $C_1$-$C_3$ alkyl; and
Z is $Cl^-$, $Br^-$, $I^-$, $BF_4^-$, $CF_3SO_3^-$, or $(CF_3SO_2)_2N^-$; and
R, R', and R" are unsubstituted.

5. The salts according to claim 4, wherein the salts are in a liquid crystal form.

* * * * *